(12) United States Patent
Blaho (10) Patent No.: US 8,778,331 B2
(45) Date of Patent: Jul. 15, 2014

(54) METHOD OF DETERMINING SUSCEPTIBILITY OF A TUMOR CELL TO A CHEMOTHERAPEUTIC AGENT: NOVEL USE OF HERPES SIMPLEX VIRUS

(75) Inventor: John Blaho, New York, NY (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 472 days.

(21) Appl. No.: 12/459,332

(22) Filed: Jun. 30, 2009

(65) Prior Publication Data

US 2009/0325146 A1    Dec. 31, 2009

Related U.S. Application Data

(60) Provisional application No. 61/133,478, filed on Jun. 30, 2008.

(51) Int. Cl.
*A61K 39/245*    (2006.01)
*C12N 15/38*    (2006.01)

(52) U.S. Cl.
USPC ..................................... 424/93.3; 435/320.1

(58) Field of Classification Search
CPC ............. A61K 35/763; C12N 15/8695; G01N 2800/52; C12Y 601/01006
See application file for complete search history.

(56) References Cited

U.S. PATENT DOCUMENTS

| | | | |
|---|---|---|---|
| 5,270,172 A | 12/1993 | Morgan | |
| 5,366,885 A | 11/1994 | Barranco, III | |
| 6,573,090 B1 * | 6/2003 | Breakefield et al. | ....... 435/320.1 |
| 6,949,359 B1 | 9/2005 | Sims | |
| 7,344,829 B2 | 3/2008 | Fidler | |
| 2002/0187126 A1 * | 12/2002 | Blaho et al. | .................. 424/93.2 |
| 2006/0172305 A1 | 8/2006 | Tidmarsh | |
| 2010/0316609 A1 * | 12/2010 | Dewhurst et al. | ............ 424/93.2 |

FOREIGN PATENT DOCUMENTS

WO    WO02/088327    * 11/2002

OTHER PUBLICATIONS

Zachos et al. J. Virol. 2001, vol. 75, No. 6, pp. 2710-2728.*
Aubert, Martine and Blaho, John, Journal of Virology, vol. 73, No. 4 Apr. 1999, pp. 2803-2813.
Aubert, Martine and Blaho, John, Microbes and Infection, vol. 3, 2001, pp. 859-866.
Aubert, Martine, et al., Apoptosis, vol. 12, 2007, pp. 19-35.
Aubert, Martine and Blaho, John, Gene Therapy, vol. 10, 2003, pp. 1437-1445.
Aubert, Martine, et al., Journal of Virology, vol. 73, No. 12 Dec. 1999, pp. 10359-10370.
Blaho, John A., et al., Current Protocols in Microbiology, 2005, pp. 14E.1.1-14E.1.23, John Wiley & Sons, Inc.
Goodkin, Margot L., et al., International Reviews of Immunology, vol. 23, 2004, pp. 141-172.
Kraft, Rachel M., et al., Virus Research, vol. 120, 2006, pp. 163-175.
Nguyen, Marie L. and Blaho, John A., Advances in Virus Research, vol. 69, 2007, pp. 67-97.
Nguyen, Marie L., et al., Journal of General Virology, vol. 88, 2007, pp. 1866-1875.
Nguyen, Marie L., et al., Virology, vol. 336, 2005, pp. 274-290.
Sanfilippo, Christine M., et al., Journal of Virology, vol. 78, No. 1 Jan. 2004, pp. 224-239.
Yedowitz, Jamie C. and Blaho, John A., Virology, vol. 342, 2005, pp. 297-310.
Leopardi, Rosario and Roizman, Bernard, Proc. Natl. Acad. Sci., vol. 93, 1996, pp. 9583-9587.
Leopardi, Rosario, et al., Proc. Natl. Acad. Sci., vol. 94, 1997, pp. 7891-7896.
Soliman, Tarik M., et al., Journal of Virology, vol. 71, No. 12 Dec. 1997, pp. 9188-9197.
Jerome, Keith R., et al., The Journal of Immunology, vol. 167, 2001, pp. 3928-3935.
Jerome, Keith R., et al., Journal of Virology, vol. 73, No. 11 Nov. 1999, pp. 8950-8957.
Koyama, A. Hajime and Adachi, Akio, Journal of General Virology, vol. 78, 1997, pp. 2909-2912.
Koyama, A. Hajime and Miwa Yoshihiro, Journal of Virology, vol. 71, No. 3 Mar. 1997, pp. 2567-2571.

* cited by examiner

*Primary Examiner* — Bao Li
(74) *Attorney, Agent, or Firm* — Siu K. Lo, Esq.

(57) ABSTRACT

The present invention provides a method of determining if a tumor cell is susceptible to killing by a chemotherapeutic agent, comprising: (a) providing a tumor cell; (b) infecting said tumor cell with a herpes simplex virus or a herpes simplex virus defective in an immediate early gene selected from the group consisting of ICP27, ICP4, and ICP22; and (c) determining the presence of apoptotic killing of said tumor cell, wherein the presence of apoptotic killing is indicative of susceptibility to said chemotherapeutic agent. Chemotherapeutic agent may include doxorubicin, etoposide, paclitaxel, cisplatin, or 5-fluorouracil. The present invention also provides a herpes simplex virus promoter construct having a lacZ gene to assess tumor resistance to chemotherapeutic agents.

11 Claims, 4 Drawing Sheets

METHOD OF DETERMINING SUSCEPTIBILITY OF A TUMOR CELL TO A CHEMOTHERAPEUTIC AGENT: NOVEL USE OF HERPES SIMPLEX VIRUS

CROSS-REFERENCE TO RELATED APPLICATIONS

The present application claims the benefit of priority under 35 U.S.C. §119(e) to U.S. Provisional Application No. 61/133,478 filed Jun. 30, 2008.

FIELD OF THE INVENTION

The present application relates generally to a method of determining tumor cell susceptibility to a chemotherapeutic agent; more particularly, the present invention relates to using a herpes simplex virus mutant lacking an immediate early gene in determining tumor cell susceptibility to a chemotherapeutic agent.

BACKGROUND OF THE INVENTION

Chemotherapeutic agents are frequently used in the clinical treatment of many forms of tumors. Information regarding whether a given tumor cell is susceptible (i.e., sensitive) or resistant to a particular chemotherapeutic agent is critical. Provided in advance, this information greatly enhances a physician's ability to implement proper dosages to kill the tumor cells. In addition, such information permits swift changes in treatment regimes and therefore avoids toxic side effects of the chemotherapeutic agent if the tumor cell proves to be chemotherapy resistant. Where a given tumor is initially sensitive to chemotherapy agents but develops resistance over the course of treatment, it becomes necessary to gain information about the susceptibility change.

There have been several disclosed tests whose goals are to predict tumor sensitivity to chemotherapy agents. One early test is based on the observation in 1954 that the ability of chemotherapy agents to reduce cellular metabolism could be monitored by measuring tetrazolium blue reduction by fresh tumor biopsy materials. (Black et al., *J. Nat'l Cancer Inst.* 14, 1147-1158 (1954)). Most other tests correlate chemo-sensitivity to a particular intracellular chemical. For example, U.S. Pat. No. 5,366,885 discloses the use of elevated glutathione to predict tumor drug sensitivity. To overcome false-negative or false-positive results, however, a four-tiered confirmatory testing is required. This cumbersome biochemical tests render the approach undesirable.

U.S. Pat. No. 5,270,172 discloses an in vitro method that utilizes estrogen and anti-estrogen and requires quantifying cell growth inhibition under these culture conditions. U.S. Patent Appl. No. 2006/0172305 discloses a method of measuring susceptibility via a glucose transporter. U.S. Pat. No. 6,949,359 discloses chemosensitivity determination using one marker whose specific binding capability to phosphatidylserine can be detected. U.S. Pat. No. 7,344,829 discloses a method for detecting the efficacy of anti-cancer treatment by comparing growth factor receptor phosphorylation. While all these assays may provide a measure of predictability to the question of tumor drug resistance, they often require long assay duration and lack reliability. Thus, there exists an unfulfilled need for a predictive assay for drug resistance, which provides rapid, reliable results for a spectrum of possible chemotherapy agents.

A method of determining drug susceptibility profile for a particular tumor (prior to the administration of chemotherapy agents) is highly desirable. However, there has been no suggestion in the art relating to a method of using virus as a means to determine tumor cell susceptibility to chemotherapy agents. There has also been no information relating the application of herpes simplex virus as a vehicle to assess drug susceptibility. The present inventors have surprisingly discovered that herpes simplex virus lacking an immediate early gene is a novel and reliable indicator for use in determining tumor cell susceptibility to chemotherapeutic agents.

SUMMARY OF THE INVENTION

The present invention provides a method of determining if a tumor cell is susceptible to apoptotic killing by a chemotherapeutic agent using a herpes simplex virus lacking an immediate early gene. Preferably, the herpes simplex virus lacks ICP27, ICP4 or ICP22.

In one aspect, the present invention provides a method of determining susceptibility of a tumor cell to apoptotic killing by a chemotherapeutic agent, comprising the steps of: (a) providing a tumor cell; (b) infecting said tumor cell with a herpes simplex virus-1 lacking an immediate early gene selected from the group consisting of ICP27, ICP4, and ICP22; and (c) determining the presence of apoptotic killing of said infected tumor cell, wherein the presence of apoptotic killing is indicative of susceptibility of said tumor cell. Preferably, the chemotherapeutic agent is doxorubicin, etoposide, paclitaxel, cisplatin, or 5-fluorouracil.

In another aspect, the absence of apoptotic killing of said infected tumor cell is indicative of resistance of said tumor cell to a chemotherapeutic agent.

In another aspect, the tumor cell is derived from a source of pancreas, colon, prostate, brain, skin, cervix, liver or stomach. Preferably, the tumor cell is derived from breast, brain or cervix. More preferably, the tumor cell is derived from breast.

In another aspect, the infecting step is performed using a herpes simplex virus-1 lacking immediate early gene of ICP27.

In another aspect, the determining step is performed by analyzing one morphological alternation including cell shrinkage, membrane blebbing, or chromatin condensation. Preferably, determining step is performed by analyzing chromatin condensation.

In an alternative aspect, the determining step is performed by measuring death factor including poly(ADP-ribose) polymerase, caspase 3, or DNA fragmentation factor-45. Preferably, the determining step is performed by measuring poly (ADP-ribose) polymerase.

In yet another aspect, the present invention provides a herpes simplex virus report construct, comprising: (a) a herpes simplex virus immediate early gene promoter, said gene promoter is selected from the group consisting of ICP27, ICP4, and ICP22; and (b) a lacZ gene, wherein said gene promoter is operably linked to said lacZ gene.

In another aspect, the present invention also provides a herpes simplex virus hosting the reporter construct.

In another aspect, the present invention provides a method of using a herpes simplex virus report construct, comprising the steps of: (a) providing a tumor cell; (b) infecting said tumor cell with said herpes simplex virus hosting the reporter construct; and (c) determining lacZ gene activity of the reporter construct. Preferably, the determining step is performed by β-galactosidase staining.

In another aspect, the present invention provides a kit, comprising: (a) a herpes simplex virus lacking an immediate early gene selected from the group consisting of ICP27, ICP4 and ICP22; (b) a reagent used to determine apoptotic killing of a herpes simplex virus infected tumor cell; and (c) an instruction, wherein said instruction detailing the use of said herpes simplex virus lacking said immediate early gene to infect a tumor cell and said reagent in determining apoptotic killing of said herpes simplex virus infected tumor cell.

Other objects, features and advantages of the present invention will become apparent from the following detailed description to those skilled in the art. It should be understood, however, that the detailed description and the specific examples, while indicating preferred embodiments of the invention, are given by way of illustration only. Various changes and modifications within the spirit and scope of the invention are encompassed by the present disclosure.

BRIEF DESCRIPTION OF THE DRAWINGS

FIG. 2 depicts immune-reactivities of apoptotic death factors. Immunoblots for death factors (PARP, DFF-45, and procaspase 3) were prepared from Hs578T tumor cells 24 hour post infection with HSV-1(KOS), wtHSV, in the presence (+) or absence (−) of cycloheximide (CHX). The 116,000 molecular weight uncleaved and 85,000 molecular weight cleaved apoptotic PARP products are observed. The anti-DFF-45 and -procaspase 3 recognize the full length forms of these proteins so loss of reactivity signal indicates apoptosis.

FIG. 4 depicts immune reactivities of apoptotic death factors. Immunoblots for death factors (PARP, DFF-45, and procaspase 3) were prepared from Hs578T tumor cells 24 hours post Mock infection or infection with DICP27. The 116,000 molecular weight uncleaved and 85,000 molecular weight cleaved apoptotic PARP products are observed. The anti-DFF-45 and procaspase 3 recognize the full-length forms of these proteins so loss of reactivity signal indicates apoptosis.

DETAILED DESCRIPTION THE INVENTION

Definitions

As used herein, the term "a" or "an" means one or more.

As used herein, the term "apoptosis" refers to a process of programmed cell death that occurs in multi-cellular organisms. Apoptosis involves a series of biochemical events such as appearance of cell death factors (e.g., poly (ADP-ribose) polymerase, caspase 3, DNA fragmentation factor-45 and the like). These biochemical events are associated with characteristic cell morphology and cell death. Specifically, morphological changes of apoptotic cells include cell shrinkage, membrane blebbing, membrane asymmetry, nuclear fragmentation, and chromatin condensation. Apoptosis is distinct from necrosis. The term "apoptotic killing" refers to killing of a target cell (e.g., tumor cell) by apoptosis. For purposes of this invention, apoptotic killing is mediated by infecting a target cell with a herpes simplex virus lacking an immediate early gene.

As used herein, the term "death factor" refers to one of the several cellular factors, generally protein based, which facilitate the apoptotic process, such as caspase 3, DFF, and PARP. In addition, "death factor processing" refers to the detection of proteolytic cleavage of the death factor protein as determined by immunoblotting methods. As such, detection of death factor processing represents validation that apoptotic cell death, apoptosis, has occurred in the cells.

As used herein, the term "poly(ADP-ribose) polymerase" (PARP) refers to a protein involved in a number of cellular processes involving mainly DNA repair and apoptosis. PARP-1 is the principal member of the PARP enzyme family and is an abundant nuclear protein in mammalian cells. PARP-1 catalyses the formation of poly (ADP-ribose) (PAR) polymers using $NAD^+$ as substrate. Upon DNA damage, PARP-1 binds rapidly to a DNA single-strand break and catalyses the addition of negatively charged PAR chains to itself (automodification) and other proteins. Thus, PARP is crucial in repairing of single-strand DNA nicks.

As used herein, the term "caspase 3" is a caspase protein which interacts with caspase 8 and caspase 9. Caspase 3 protein is a member of the cysteine-aspartic acid protease (caspase) family.

As used herein, the term "chemotherapeutic agent" refers to a chemical agent that is used in a chemotherapy treatment in a patient that has a tumor cell. A chemotherapeutic agent generally includes alkylators, anthracyclines, radionucleotides, enzyme inhibitors, aromatase inhibitors, biphosphonates, cyclo-oxygenase inhibitors, estrogen receptor modulators, folate antagonists, inorganic arsenates, microtubule inhibitors, modifiers, nitrosoureas, nucleoside analogs, orthoclase inhibitors, platinum-containing compounds, retinoid, topoisomerase 1 inhibitors, topoisomerase 2 inhibitors, or tyrosine kinase inhibitors.

As used herein, the term "tumor cell" includes, but is not limited to, tumor cells derived from a source of breast, prostrate, colon, pancreas, brain, liver, skin, stomach, cervix, uterus, or the like.

As used herein, multiplicity of infection (MOI) is the ratio of infectious agents (e.g. herpes simplex virus) to infection targets (e.g., tumor cells). For example, when referring to a group of cells inoculated with infectious virus particles (plaque-forming units; pfu), the multiplicity of infection or MOI is the ratio defined by the number of infectious virus particles divided by the number of target cells present. MOI often ranges from 0.1-10.0 pfu/cell.

As used herein, the term "immediate early gene" is defined as a virus gene immediately express upon virus infection of a target. This includes ICP4, 22 and 27. HSV-1 genome has been sequenced and publicly available in Genbank (NC_001806 (Locus: HE1CG; Accession numbers: X141112, D00317, D00374, S40593). ICP27 has a Gene name of UL54; Locus tag HHV1gp079, protein_id="NP_044657.1." ICP4 has a Gene name of RS1; Locus tag HHV1gp084, protein_id="NP_044662.1" ICP22 has a Gene name of US1; Locus tag HHV1gp085, protein_id="NP_044663.1."

As used herein, the term "operable linked" refers that a first gene element (such as a promoter) to be in operable linkage with a second gene element (such as a lacZ gene) in a manner that the first gene element modulates the expression of the second gene element (increasing or decreasing expression, as appropriate). The present invention therefore provides an immediate early promoter of viral genes (e.g., ICP4, ICP22 or ICP27) "operably linked" to a reporter gene element (e.g., lacZ gene). Specifically, lacZ gene was genetically engineered into a recombinant plasmid DNA construct in such a way that it is biologically expressed and functional when introduced into a mammalian cell in culture. When lacZ is operably linked to a gene expression promoter region, the DNA tract contains the necessary sequence information required for its association with relevant cellular transcription factors.

The present invention provides a method of determining tumor cell susceptibility to chemotherapeutic agents with the use of herpes simplex virus as well as herpes simplex virus lacking an immediate early gene (e.g., ICP27, ICP4 or ICP22). The present inventor discovered that tumor cells that are resistant to HSV-induced apoptotic killing are also resistant to chemotherapeutic agent-mediated apoptotic killing. In other words, tumor cells that are susceptible to HSV-mediated apoptotic killing could be killed by chemotherapeutic agents, such as doxorubicin, etoposide, and the like.

Without being bound by any particular theory, we hypothesize that the susceptibility of tumor cells to HSV-dependent apoptotic killing requires that these cells may possess a functional ability to undergo apoptosis. As such, tumor cells may require the machinery of the mitochondrial-dependent apoptotic cascade. The present invention provides that a HSV-dependent apoptosis technology that can be used to monitor cellular signaling and metabolic pathways and therefore, to determine tumor cell susceptibility to anti-tumor drugs (i.e., chemotherapeutic agents, such as doxorubicin, etoposide, paclitaxel, cisplastin, 5-FU and the like).

The present invention provides a novel approach of using herpes simplex virus lacking an immediate early gene to induce tumor cell apoptotic killing and correlate it with chemotherapeutic resistance. It is contemplated that viruses for the present invention will be those that are sufficient to induce tumor cell apoptotic killing. An exemplary virus includes the herpes simplex virus, which in turn encompasses herpes simplex virus-1 and herpes simplex virus-2. Protein synthesis inhibitor is required when herpes simplex viruses (i.e., HSV-1 and HSV-2) are used. Exemplary protein synthesis inhibitor includes cycloheximide, puromycin, and the like. Optimal doses of cycloheximide or puromycin can conveniently be determined to prevent protein synthesis in tumor cells. Preferably, a dose of cycloheximide of 10 µg/ml is used.

It is also contemplated that modified herpes simplex viruses are included. The modification, deletion of an immediate early gene, results in a replication defective HSV (rdHSV). These modified HSV cannot replicate in cells after infection, due to its inability to complete its replication cycle while inducing apoptotic killing of the infected tumor cell.

In one embodiment, the present invention encompasses HSV deleted for ICP27; other preferred virus is one that has been deleted in ICP4 or IC22. Viruses deleted in one or more of the genes listed above will also be particularly useful for inducing apoptotic killing in tumor cells in the present invention. When rdHSV is used, protein synthesis inhibitor is not required in order to induce apoptotic killing in tumor cells.

In one embodiment, the present invention provides a method of using an amount of a herpes simplex virus to infect tumor cells (i.e., effectively induce apoptotic killing in tumor cells). Preferably, the MOI for infecting tumor cells ranges from 0.1 pfu/cell to 10.0 pfu/cell. Preferably, MOI ranges from 1 pfu/cell to 5 pfu/cell. More preferably, MOI is 5 pfu/cell.

Preferably, a tumor cell is derived from a mammal. Preferably, the mammal is a human. In one embodiment, tumor cells may be surgically excised and put into culture media (e.g., DMEM+10% FBS) for a brief period of time (i.e., <24 hours). The obtained tumor cells may then be infected by HSV-1 mutants (e.g., HSV-1 lacking an immediate early gene) and apoptotic killing may be determined in accordance with the protocols described herein.

In specific embodiments, the mammal has a tumor of a tissue or organ derived from brain, lung, liver, spleen, kidney, blood cells, pancreas, colon, breast, cervix, prostate, skin, and the like. Preferably, the tumor cell is derived from breast, colon and cervix. More preferably, the tumor cell is derived from breast. In addition, the tumor cells may have a defective p53 (e.g., colon tumor cells).

Tumor cell susceptibility towards HSV-1 mutant (e.g., ΔICP4, ΔICP22, or ΔICP27) is evaluated. If there is HSV-mediated apoptotic killing, it is concluded that the tumor cell may also be susceptible towards chemotherapeutic agents. Relying on the present inventive assay, a physician may conveniently determine if a particular cancer patient would respond to a chemotherapeutic agent. The present invention thus provide a rapid, non-invasive and reliable assay in determining if a cancer patient may respond to chemotherapy. Another advantage of the present invention is that the assay assists a physician to tailor particular needs for a cancer patient (i.e., personal medicine).

The chemotherapeutic agent includes, but is not limited to cisplatin, 5-fluorouracil, mitomycin, etoposide, camptothecin, actinomycin-D, doxorubicin, verapamil, podophyllotoxin, daunorubicin, vincristine, vinblastine, melphalan cyclophosphamide, tumor necrosis factor, taxol and bleomycin. Preferably, the chemotherapeutic agent is doxorubicin, etoposide, paclitaxel, cisplatin, or 5-fluorouracil.

One clear advantage of this aspect of the invention involves treatment of tumors in which some cells are p53-positive while others are p53-negative. Apoptotic killing is hypothesized to act through two major pathways. One is mediated via a death receptor, such as Fas or tumor necrosis factor receptor. Once the receptor binds ligand, it then recruits an adaptor molecule that allows the binding and autocleavage/activation of procaspase-8. Activated caspase-8 induces a cascade, which includes processing of effector caspases (executioners) caspase-3 and caspase-7.

The other is mediated by mitochondria release of cytochrome C into the cytoplasm, where it associates with Apaf-1 and permits the recruitment and activation of caspase-9. This, in turn, also leads to the cascade of events culminating in the activation of the executioners of apoptotic killing. In both pathways, caspase cleavage ultimately leads to the morphological and biochemical features characteristic of apoptotic killing, including apoptotic body formation, cell shrinkage, membrane blebbing, chromatin condensation, and DNA fragmentation. Among the cleavage targets are the DNA repair enzyme poly(ADP-ribose) polymerase (PARP) and the DNA fragmentation factor-45 (DFF-45). Thus, the process of apoptotic killing generally involves the processing of caspase-3, DFF-45, and PARP.

Apoptotic killing features include chromatin condensation, fragmentation of nuclei, membrane blebbing, and the formation of apoptotic bodies. Assays for monitoring apoptotic killing are well known to those of skill in the art and include for example, monitoring cell shrinkage, nuclear condensation, monitoring appearance of genomic DNA fragmentation ladders; monitoring the processing of PARP, a 116 kDa protein, which generates an 85 kDa product which may be detected by the anti-PARP antibody (Aubert et al., *J. Virol.* 1999, 73:10359-70); and monitoring apoptosis-induced processing of DFF (45 kDa) and caspase-3 (32 kDa) as determined by the loss of reactivity with the anti-DFF-45 and anti-caspase-3 antibodies.

The method of the present invention is useful for monitoring the effects of therapeutic agents in treating cancer. In one embodiment of the invention, there is provided a method for assessing the efficacy of a therapeutic compound (e.g., 5-FU, cisplatin and the like) for the treatment of a tumor disease.

Protocols for obtaining tumor cells from a cancer patient (from a source such as pancreas, colon, cervix, liver, breast and the like) are established, and a physician can conveniently apply the present assay using the tumor cells derived from the various tumor cells.

The present invention comprises the steps of (i) obtaining a tumor cell from a cancer patient; (ii) infecting the tumor cell with HSV-1 or HSV-2 lacking an immediate early gene (i.e., ICP4, ICP22, or ICP27); and (iii) determining the presence of apoptotic killing of the tumor cell mediated by the HSV mutants. If there is presence of apoptotic killing of the tumor cells, it is indicative of efficacy of a chemotherapeutic compound in treating the patient of the cancer disease.

The present invention also provides a herpes simplex virus report construct, comprising a herpes simplex virus containing (i) a herpes simplex virus immediate early promoter; and (ii) a lacZ gene, wherein said herpes simplex virus lacks gene lacking an immediate early gene selected from the group consisting of ICP27, ICP4, and ICP22, and said promoter is operably linked to said lacZ gene.

The present invention provides a method of using a herpes simplex virus report construct, comprising the steps of: (i) providing a tumor cell; (ii) infecting said tumor cell with a herpes simplex virus report construct having an immediate early promoter operably linked to a lacZ gene; (iii) determining the activity of said lacZ gene; wherein the positive activity of said lacZ gene is indicative of tumor cell resistance to chemotherapeutic agents, and the negative activity of said lacZ gene is indicative of tumor cell sensitivity to chemotherapeutic agents.

Chemotherapy Resistance Measurement Kit

In one embodiment, the present invention provides a kit for screening patient tumors to determine susceptibility to a particular chemotherapeutic agent.

Kits of the invention include reagents for assessing apoptotic killing, herpes simplex virus (including HSV-1 and HSV-2) and herpes simplex virus that is deficient in immediate early gene replication (i.e., lacking ICP27, ICP4, and ICP22), instructions that details the use of the herpes simplex virus-1 in inducing apoptosis of tumor cells and conditions whereby extent of apoptotic killing can be measured. In one embodiment, the kit contains fluorescence probe specific for measuring apoptotic killing of tumor cells. The kit of the invention may optionally comprise additional components useful for performing the methods of the invention, such as devices for use in isolating tumor cells from blood source of a patient. In addition, the kits may contain calibration curves, a reference sample (a reference tumor cell and herpes simplex virus-1) for comparison to a reference value as described herein. Kits can conveniently be provided in an array format, for example, in multi-well plates.

EXPERIMENTS

Example 1

Figure 1:
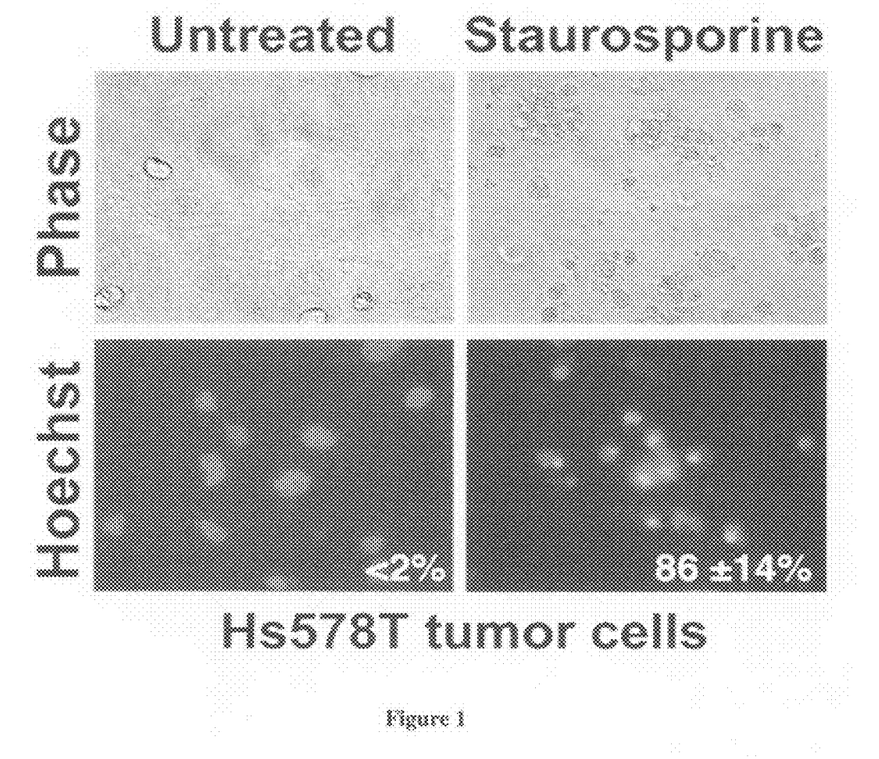
FIG. 1 depicts phase contrast (top) and Hoechst fluorescence (bottom) images of Hs578T tumor cells. Hs578T tumor cells were visualized at 24 hours after either no treatment (control) or treatment with staurosporine (STS) (40× magnification). Values in the lower right corner of Hoechst panels denote the mean and standard deviation of the percentage (%) of nuclei containing condensed chromatin from three (3) independent experiments.

Herpes Simplex Virus Induces Apoptotic Killing in Tumor Cells a) Tumor Cell Apoptosis We have established an in vitro cell model and examined herpes simplex virus-induced apoptotic killing of tumor cells. In the first series of studies, we used a standard inducer of apoptotic killing. A protein kinase inhibitor (i.e., staurosporine) was used. Mammary tumor cells (Hs578T) were cultured and treated with staurosporine (0.1-2 µM) for about 12-18 hours. Staurosporine caused Hs578T cells to undergo morphological alternations consistent with apoptotic killing (i.e., cell shrinkage, chromatin condensation, and membrane blebbing) as compared to untreated cells. (FIG. 1). When this phenotype was quantified for three independent experiments, the staurosporine-treated Hs578T cells exhibited 86±14% chromatin condensation.

Figure 2:
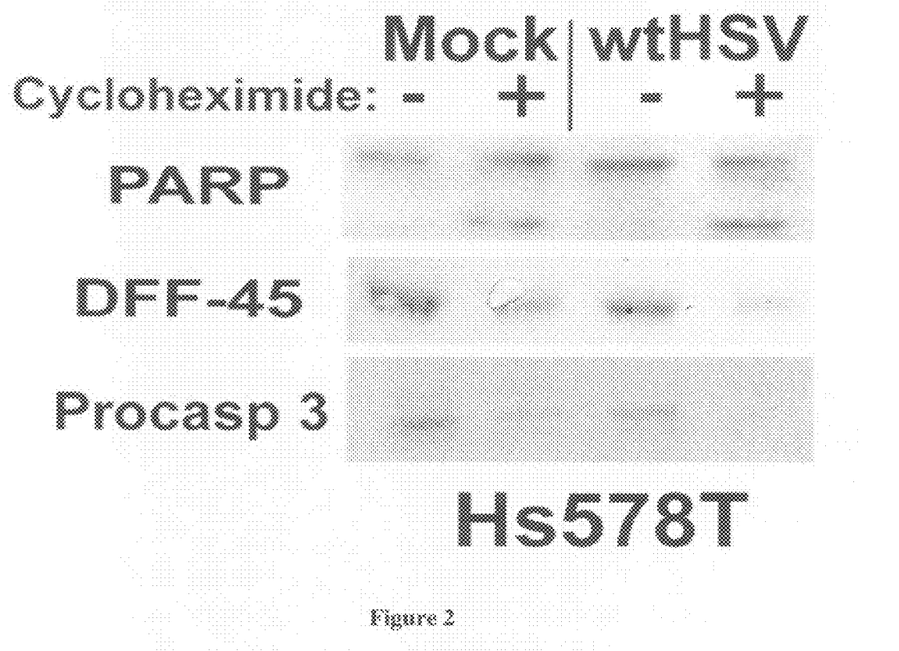

In addition, staurosporine caused drastic death factor processing [poly(ADP-ribose) polymerase, procaspase 3, and DNA fragmentation factor-45] in Hs578T cells (FIG. 2). Thus, we established an in vitro system showing that Hs578T tumor cells are capable of undergoing apoptotic killing.

b) HSV-1 Induces Apoptotic Killing in Tumor Cells

Using Hs578T cells, we next examined whether herpes simplex virus (HSV) can induce apoptotic killing in these tumor cells. Standard methods were used to prepare wild-type HSV-1 (i.e., wtHSV-1). (Blaho et al.: Herpes Simplex Virus: Propagation, Quantification, and Storage. *Current Protocols in Microbiology*. Wiley & Sons. 14:1-23, 2005). Hs578T cells were infected with wtHSV-1 and examined for tumor cell apoptotic killing. A range of wtHSV-1 concentration was used and we observed that one particle of wtHSV-1 was sufficient to induce apoptotic killing of a tumor cell. Apoptotic killing was evaluated at 24-hour post infection by monitoring morphological alternations and presence of death factor processing as detailed above.

wtHSV-1 infected Hs578T cells (in the presence of 10 µg/ml cycloheximide) caused drastic death factor processing (poly(ADP-ribose) polymerase, procaspase 3, and DNA fragmentation factor-45) (FIG. 2). Not wishing to be bound by any theory, we observed that the inhibition of protein synthesis (e.g., cycloheximide) during wtHSV-1 infection would permit apoptotic killing to occur. In addition, wtHSV-1 infection caused morphological alternations consistent with apoptotic killing (data not shown). Mock-infected Hs578T cells exhibited flat cell shapes and were well spread-out. The nuclei in the mock-infected cells exhibited homogenous Hoechst staining (data not shown). Cycloheximide alone had no apparent apoptotic effects in Hs578T cells (data not shown).

These results demonstrate that wtHSV-1 induces apoptotic killing in Hs578T cells.

c) HSV-2 Induces Apoptotic Killing in Tumor Cells

We also examined if a different type of herpes simplex virus (i.e., HSV-2) may induce apoptotic killing of tumor cells. Standard methods were used to prepare wild-type HSV-2 (i.e., wtHSV-2). (Blaho et al.: Herpes Simplex Virus: Propagation, Quantification, and Storage. *Current Protocols in Microbiology*. Wiley & Sons. 14:1-23, 2005). Tumor cells (human carcinoma HEp-2) were used and infected with wtHSV-2. The results indicate that, like wtHSV-1, wtHSV-2 (in the presence of 10 µg/ml cycloheximide) induces apoptotic killing of HEp-2 cells. In particular, wtHSV-2 caused both the morphological alternations and death factor processing (data not shown). These results with wtHSV-1 and wtHSV-2 are summarized in Table 1. Thus, infection of Hs578T and HEp-2 cells with wtHSV-1 and wtHSV-2, respectively, leads to substantial apoptotic killing of tumor cells.

TABLE 1

Herpes Simplex Virus Induces Apoptosis in Tumor Cells

| Treatments | Morphological Alternations Cell, shrinkage, Membrane blebbing, Condensed Chromatin | Death Factor Processing Poly(ADP-ribose) Polymerase, Procaspase 3, and DNA Fragmentation Factor-45 |
|---|---|---|
| Staurosporine | + | + |
| wtHSV-1 + cycloheximide | + | + |
| wtHSV-2 + cycloheximide | + | + |

Example 2

HSVs Lacking Immediate Early Genes Induce Tumor Apoptotic Killing

Herpes simplex virus contains a total of five (5) immediate early genes, of which three (3) are essential for viral replication (i.e., ICP27, ICP4 and ICP22). We prepared ICP27-, ICP4-, and ICP22-null recombinant viruses (i.e., ΔICP27, ΔICP4, ΔICP22) using standard methods. (Sanfilippo et al. ICP0 gene expression is a HSV-1 apoptotic trigger. *J. Virol.* 78: 6810-6821, 2006). The characteristics of these deletion mutants are summarized in Table 2.

TABLE 2

Herpes Simplex Virus Deletion Mutants

| HSV Deletion Mutants | Genes Deleted | Characteristics |
|---|---|---|
| ΔICP27 | UL54 | Defective in viral DNA synthesis and late gene expression |
| ΔICP4 | Alpha4 | Defective in viral early and late gene expression |
| ΔICP22 | US1, alpha22 | Defective in viral late gene expression | a) ΔICP27 Induces Apoptotic Killing in Tumor Cells

Figure 3:
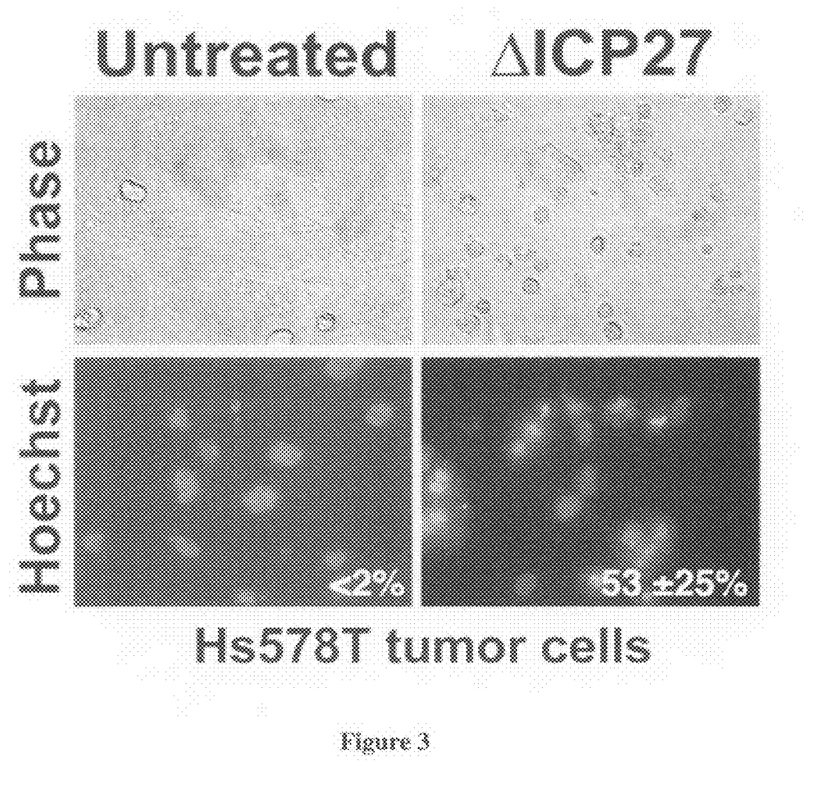
FIG. 3 depicts phase contrast (top) and Hoechst fluorescence (bottom) images of DICP27 infected Hs578T tumor cells. Hs578T tumor cells were visualized at 24 hours after either no treatment or infection with DICP27 (40× magnification). The values in the lower right corner of Hoechst panels denote the mean and standard deviation of the percentage (%) of nuclei containing condensed chromatin from three (3) independent experiments.
Figure 4:
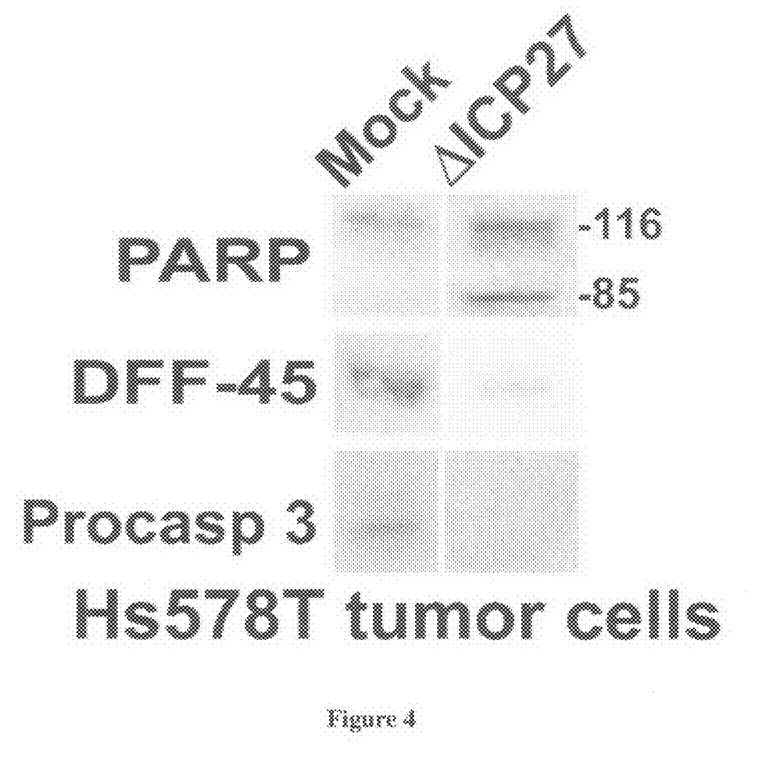

In this study, we examined whether herpes simplex virus lacking an immediate early gene (e.g., ΔICP27) would induce apoptotic killing of Hs578T tumor cells. Fifty-three percent (53%) of the Hs578T cells, when infected with ΔICP27, exhibited membrane blebbing and chromatin condensation (FIG. 3). Additionally, the ΔICP27-infected Hs578T cells displayed PARP cleavage and had lower levels of DFF-45 and procaspase 3 as compared to mock-infected cells (FIG. 4). These results demonstrate that infection of Hs578T cells with HSV lacking an immediate early gene (e.g., ΔICP27) sufficiently leads to tumor apoptotic killing. Thus, viruses deleted for the major viral regulatory protein ICP27 resulted in apoptotic cell death of the tumor cell.

b) ΔICP4 Induces Apoptotic Killing in Tumor Cells

Infection of HEp-2 cells with ΔICP4 caused the tumor cells to undergo apoptotic killing as evidenced by morphological and biological changes and death factor processing (data not shown).

c) ΔICP22 Induces Apoptotic Killing in Tumor Cells

Infection of HEp-2 cells with ΔICP22 similarly caused the tumor cells to undergo apoptotic killing as evidenced by morphological and biological changes and death factor processing (data not shown). In conclusion, these data indicate that HSV lacking immediate early genes can induce apoptotic killing in tumor cells. (See, Table 3)

TABLE 3

Herpes Simplex Virus Deletion Mutants Induce Apoptotic Killing in Tumor Cells

| HSV Deletion Mutants | Morphological Alternations Cell, shrinkage, Membrane blebbing, Condensed Chromatin | Death Factor Processing Poly(ADP-ribose) Polymerase, Procaspase 3, and DNA Fragmentation Factor-45 |
|---|---|---|
| ΔICP27 | + | + |
| ΔICP4 | + | + |
| ΔICP22 | + | + |

Example 3

HSV Induces Apoptotic Killing in Additional Tumor Cells a) HSV Induces Apoptosis in Colon, Brain and Breast Tumor Cells So far, we have demonstrated HSV induces apoptotic killing in Hs578T (mammary cancer cells) and HEp-2 cells (epithelial carcinoma). To gain further insight into the tumor cell determinants for susceptibility to HSV-induced apoptotic killing, we analyzed a selected group of tumor cells. In this study, we used both wtHSV-1 and ΔICP27 and representative tumor cells. Experiments were conducted using conditions described above. Table 4 summarizes the results using .ΔICP27:

TABLE 4

Herpes Simplex Virus Induce Apoptotic Killing in Several Tumor Cells

| HSV | Types of Tumor Cells | Apoptotic Killing (measured by morphological alternations and death factor processing |
|---|---|---|
| ΔICP27 | Colon Tumor | |
| | HT-29 | + |
| | RKO | + |
| | RKO-E6 | + |
| | Brain Tumor | |
| | SK-N-SH | + |
| | Breast Tumor | |
| | MCF-7/C3 | + |

Similar results were obtained when wtHSV (in the presence of cycloheximide) was used (data not shown). From these results, we conclude that certain colon and brain tumor derived cells can respond to HSV induced apoptotic killing.

b) HSV Fails to Induce Apoptotic Killing in Some Tumor Cells

We discovered that not all tumor cells tested were susceptibility to killing by HSV. The inability to induce apoptotic killing does not relate to the absence of immediate early genes in HSV (e.g., ΔICP27) because wtHSV-1 also fails to induce apoptotic killing in these cells (data not shown). These results suggest that the susceptibility of HSV-induced apoptotic killing may relate to intrinsic properties of the tumor cells and is not dependent on the virus. The underlying mechanism is presently not known and one of ordinary skill in the art would not be able to predict if a particular tumor cell may be sensitive or resistant to HSV-induced apoptotic killing.

TABLE 5

Herpes Simplex Virus Did Not Induce Apoptosis in Certain Tumor Cells

| HSV | Types of Tumor Cells | Apoptotic Killing (measured by morphological alternations and death factor processing) |
|---|---|---|
| ΔICP27 | Prostate Tumor PC3 | – |
|  | Brain Tumor U373 | – |
|  | Breast Tumor MCF-7 | – |

These results indicate that certain tumor cells such as PC-3, MCF-7, and U373 are resistant to HSV induced apoptotic killing.

Example 4

HSV-Dependent Apoptotic Killing in Tumor Cells Requires Mobilization of Mitochondrial Cytochrome C There are at least two known apoptotic pathways. The first pathway is initiated by the extracellular (extrinsic) binding of a death ligand to its receptor on the cell surface; while the second pathway integrates intracellular apoptotic signals through a mitochondrial (intrinsic) route. We showed that HSV-dependent apoptotic killing may involve the second pathway (i.e., mitochondrial apoptotic pathway) in tumor cells. To this end, we showed that: (i) ΔICP27 infected HEp-2 tumor cells had release cytochrome c from mitochondria; and (ii) addition of caspase-9-specific inhibitor prevented HSV-induced apoptotic killing in HEp-2 cells (data not shown). Because caspase-9 is activated by released cytochrome c, these findings suggest that HSV induces apoptotic killing by stimulating mitochondrial cytochrome c release.

Example 5

Chemotherapeutic Susceptibility in Tumor Cells

We examined tumor cell killing by chemotherapeutic agents. In this study, HEp-2 cells were treated with varying amounts of doxorubicin and etoposide. Apoptotic killing was measured using the method detailed above. Both doxorubicin (10 μM) and etoposide (125 μM) induce morphological alternations and death factor processing (data not shown). Thus, these tumor cells were sensitive to chemotherapeutic agents.

During our survey of the sensitivities of patient derived tumor cells to chemotherapeutic agents, we discovered that certain tumor cells (e.g., MCF-7) were resistant to drug-induced apoptosis. Altogether, we have identified chemo-resistant and -sensitive tumor cells.

Furthermore, we conducted a survey of the literature and found a group of tumor cells that are chemo-resistant or -sensitive. We examined 5-fluorouracil, cisplatin, doxorubicin, etoposide and paclitaxel because they are classical chemotherapeutic agents.

Table 6 summarizes the panel of chemo-resistant and -sensitive tumor cells from different sources.

TABLE 6

Tumor Cells That Are Known to Be Resistant or Sensitive to Chemotherapeutic Agents

|  | 5-Fluorouracil | Cisplatin | Doxorubicin | Etoposide | Paclitaxel |
|---|---|---|---|---|---|
| Melanoma (A375) | Resistant | Resistant | Resistant | Resistant | Sensitive |
| Ovarian tumor (ES-2) | Sensitive | Resistant | Resistant | Resistant | Resistant |
| Hepatic tumor (Hep3B) | Resistant | Resistant | Resistant | Resistant | Resistant |
| Hepatic tumor (SNU182) | Resistant | Resistant | Resistant | Resistant | Resistant |
| Hepatic tumor (SNU423) | Resistant | Resistant | Resistant | Resistant | Sensitive |
| Breast tumor (R193) | Sensitive | Resistant | Resistant | Resistant | Sensitive |
| Breast tumor (SKBR3) | Sensitive | Resistant | Resistant | Resistant | Sensitive |
| Pancreatic tumor (181/85P | Sensitive | Resistant | Resistant | Resistant | Sensitive |
| Gastric tumor (257P) | Resistant | Resistant | Resistant | Resistant | Sensitive |

Example 6

HSV Induced Apoptotic Killing Correlates with Chemotherapeutic Sensitivity

So far, we have established a correlation in certain tumor cells between HSV-induced apoptotic killing and chemotherapeutic susceptibility. For example, MCF-7 tumor cells were found to be resistant to doxorubicin and etoposide and also resistant to HSV-induced apoptotic killing. On the other hand, HEp-2 cells were found to be sensitive to doxorubicin and etoposide as well as HSV-induced apoptotic killing.

To further establish the correlation, we chose a large panel of patient derived breast tumor cells. More than twenty (20) tumor cell lines were obtained from patients or from a commercial source. We chose the following tumor cell mutants because they possess defined p53 mutations. We showed that Hs578Ts are sensitive to HSV-induced apoptotic killing (See, Example 2). These tumor cells are evaluated for their sensitivity to HSV-induced apoptotic killing.

TABLE 7 p53 Mutant Breast Tumor Cells

| Cell Lines | Types | Cell Lines | Types |
|---|---|---|---|
| BT20 | Missense | BT-474 | Missense |
| Hs578T | Missense | MDA-MB-231 | Missense |
| MDA-MB-435 | Missense | MDA-MB-436 | Insertion |
| MDA-MB-453 | Deletion | MDA-MB-468 | Missense |
| SK-BR-3 | Missense | T-47D | Missense |

The following breast tumor cells were specifically chosen because they possess wild type p53 (See, Table 8). These tumor cells are evaluated for their sensitivity to HSV-induced apoptotic killing.

TABLE 8

Wild type p53 Breast Tumor cells

| Cell Lines | Types | Cell Lines | Types |
|---|---|---|---|
| MCF-7 ATCC | wt | MCF-7 PV | wt |
| MCF-7 N | wt | MCF-7 P | wt |
| MCF-7 C3 | wt/caspase 3 + | MDA-MB-175-VII | wt |
| ZR-75-1 | wt | | |

Furthermore, we chose additional breast tumor cell lines, including HCC1419, HCC1954, MDA-MB-330, and UACC812. Together, these breast tumor cells establish the tumor cell susceptibility to HSV-induced apoptotic killing.

Example 7

Use of HSV Reporter Constructs to Assess Chemotherapy Resistance in Tumor Cells

We observed that tumor cells which are sensitive to HSV-dependent apoptotic killing undergo cell lysis and therefore do not allow any viral gene expression from the HSV genome. However, tumor cells which are resistant to HSV-dependent apoptotic killing, by virtue of its cell survival, allow gene expression from the HSV genome. We took advantage of this observation and used a HSV report construct to assess chemotherapy resistance in tumor cells.

We prepared a novel HSV report construct. We used an established protocol (Aubert and Blaho, *J. Virol* 73:2803-2813, 1999) and prepared ΔICP27. ΔICP27 is an ICP27-null virus that contains a replacement of the ICP27 gene with the *Escherichia coli* lacZ gene. ΔICP27 is then added to tumor cells that are either sensitive or resistant to chemotherapeutic agents. After optimal culturing, we stain for β-galactosidase to assess gene expression from the HSV genome. A positive staining would reveal the expression of the lacZ gene, which is indicative of viral gene expression and correlate with its resistance to (i) HSV-dependent apoptotic killing, and (ii) chemotherapeutic killing. On the other hand, a negative staining would reveal the lack of lacZ expression, and indicate susceptibility to HSV-dependent apoptotic killing and chemotherapeutic agents. Thus, infection of tumor cells with ΔICP27 combined with β-galactosidase staining is a useful tool to identify tumor cells that are resistant to chemotherapeutic agents.

Protocols and Reagents

CELLS FOR VIRUS PROPAGATION: African green monkey kidney (Vero) cells were obtained from the American Type Culture Collection (Rockville, Md., USA). Vero 2-2 cells represent Vero cells expressing the ICP27 protein. Vero and Vero 2-2 cells were cultured in Dulbecco's modified Eagle's medium (DMEM) and supplemented with 5% fetal bovine serum (FBS). These Vero cells were used to propagate Herpes Simplex Viruses (see below).

TUMOR CELLS: All tumor cells used in our studies were obtained from the American Type Culture Collection (Rockville, Md.). U373, SK-N-SH, MCF-7, RKO and RKO-E6 cells were maintained in Dulbecco's modified Eagle's medium (DMEM) supplemented with 10% fetal bovine serum (FBS). Hs578T cells were grown in DMEM containing 10% FBS and 0.01 mg/ml bovine insulin. HT-29 and PC-3 cells were grown in 10% FBS-containing McCoys 5a or F12K medium, respectively. HEp-2 cells were maintained in DMEM with 5% FBS.

HERPES SIMPLEX VIRUSES: Wild type HSV-1 and HSV-2 were obtained and prepared as described (Blaho et al.: Herpes Simplex Virus: Propagation, Quantification, and Storage. *Current Protocols in Microbiology*. Wiley & Sons., 14:1-23, 2005). In essence, we obtained these herpes simplex viruses from patients, and were propagated and tittered on Vero cells and used subsequently to infect tumor cells at varying MOI of 1-10. HSV-1(ΔICP27) is an ICP27-null virus derived from HSV-1 containing a replacement of the α27 gene with the *Escherichia coli* lacZ gene. ΔICP4 was derived from the HSV-1 and is an ICP4-null virus which is deleted for 3.6 kb of the coding region of ICP4 due to having the *Escherichia coli* lacZ gene inserted in place of ICP4. ΔICP22 is derived from HSV-1 and contains a complete deletion of the ICP22 gene.

PREPARATION OF HSV MUTANT STRAINS: ΔICP27 is an HSV-1 deletion mutant virus in which the ICP27 coding sequence was completely removed from the viral genome. Because ICP27 is essential for virus growth, the ΔICP27 virus was generated and propagated with Vero 2-2 cells which express ICP27 and thus complement the ICP27 deficiency. Preparation of HSV mutant strains was made by a protocol similar to those described in O'Toole et al. (Virology 305, pp. 153-167, 2003) and Pomeranz et al. (Journal of Virology 74 (21), pp. 10041-10054, 2000). ΔICP27 was generated by homologous recombination between the wild type KOS genome and a linearized plasmid containing a deletion of ICP27 but maintaining flanking sequences homologous to the KOS genome. The integrity of the deletion mutation in ΔICP27 was validated by Southern hydridization, PCR, and immunoblotting methods. Similar approaches were used for the generation of ΔICP4 and ΔICP22 HSV mutant strains.

INFECTION OF TUMOR CELLS WITH HSV MUTANTS: Approximately $1\times10^6$ cells (i.e., tumor cells) were exposed to 10 plaque forming units (PFU) per ml of ΔICP27 virus in 1 ml of 5% NBCS for 1 hour at 37° C. After this adsorption step, the medium was removed and discarded. 3 ml of fresh 5 NBCS was then added. Cells were maintained at 37° C. for at least 18 hours.

MICROSCOPIC ANALYSIS OF HSV INFECTED TUMOR CELLS: The morphology of HSV infected cells was analyzed by phase contrast and fluorescence microscopy using an Olympus IX70/IX-FLA inverted fluorescence microscope. Images were acquired using a Sony DKC-5000 digital photo camera linked to a PowerMac workstation and processed through Adobe Photoshop.

Analysis of Chromatin Condensation of HSV Infected Tumor Cells:

For visualization of chromatin condensation in live cells, 5 mg Hoechst 33258 (Sigma) per ml was added to the medium and allowed to incubate at 37° C. for 30 min. The percentage (%) of nuclei containing condensed chromatin was determined by dividing the number of brightly stained, small (condensed) nuclei by the total number of nuclei (uncondensed plus condensed) in a particular (640) microscopic field. At least 100 nuclei were counted for each data point. The percentage (%) of chromatin condensation is represented as the mean±SD of three independent experiments.

IMMUNOBLOT ANALYSIS OF HSV INFECTED TUMOR CELLS: Whole-cell protein extract was prepared using lysis buffer (50 mM Tris/HCl, pH 7.5, 150 mM NaCl, 1% Triton X-100, 1% deoxycholate, 0.1% SDS) supplemented with 2 mM PMSF (freshly prepared stock), 1% Translysol, 0.1 mM L-1-chloro-3-(4-tosylamido)-4-phenyl-2-butanone, 0.01 mM L-1-chlor-3-(4-tosylamido)-7-amino-2-heptanon-hydrochloride. Protein concentrations were determined using a modified Bradford protein assay (Bio-Rad Laboratories). Total protein (20 or 50 mg) was separated on 15% N, N9-diallyltartardiamide-acrylamide gels and electrically transferred to nitrocellulose. Pre-stained molecular mass markers were loaded and immunostaining of the actin loading control was carried out.

ANALYSIS OF APOPTOTIC DEATH FACTOR PROCESSING OF HSV INFECTED TUMOR CELLS: Cell membranes were incubated for 1 hour at room temperature in blocking buffer (PBS containing 5% non-fat, dried milk) and incubated overnight at 4° C. in primary antibody. Monoclonal antibodies specific for poly(ADP-ribose) polymerase (PARP) (PharMingen), procaspase 3 (BD Transduction) and the control actin (Sigma) and DFF-45 (Santa Cruz) were diluted at a concentration of 1:1000 in Tris buffered saline containing 0.1% Tween 20 (TBST) and 0.1% BSA. After washing in TBST, membranes were incubated with anti-mouse antibodies conjugated to alkaline phosphatase (Southern Biotech) diluted in blocking buffer (1:1000) for 1 hour at room temperature. Following washing in TBST, immunoblots were developed in buffer containing 5-bromo-4-chloro-3-indolyl phosphate and 4-nitro blue tetrazolium chloride. To quantitate the percentage (%) of total infected cell PARP that was cleaved, densitometry of immune-reactive PARP was performed. NIH IMAGE version 1.63 was used to measure the integrated density (ID) of the 116 kDa uncleaved and 85 kDa cleaved PARP bands. These values were used to calculate the percentage (%) of PARP cleavage for each lane using the following formula: Percentage (%) cleavage equals [(cleaved PARP ID) divided by (cleaved PARP ID plus uncleaved PARP ID)] times 100.

PREPARATION OF HSV CONTAINING LAC Z REPORTER CONSTRUCT: The lacZ coding sequence was isolated from plasmid pCH110 (Pharmacia, Piscataway, N.J.). A DNA restriction fragment containing the lacZ coding sequences was inserted into a plasmid such that lacZ was under the control of an HSV immediate early (IE) promoter. This reporter construct was introduced into the genome of the ΔICP27 virus by homologous recombination (as described above).

Analysis of Lacz Reporter of HSv Infected Tumor Cells:

Approximately $1 \times 10^6$ cells infected with ΔICP27 virus containing the lacZ reporter construct are washed three times with phosphate buffered saline (PBS). The cells are fixed for 5 min at 25° C. by the addition of 2% formaldehyde and 0.2% glutaraldehyde in PBS. The cells are washed again three times with PBS. LacZ activity is measured by adding 0.1 mg/ml of 5-bromo-4-chloro-3-indolyl-b-D-galactoside (X-gal) in PBS containing 5 nM potassium ferrocyanide and 5 mM ferriccyanide following incubation at 37° C. for 30 min. Number of blue cells (indicative of lacZ activity) is counted using a phase contrast microscope.

All patents, publications, gene accession numbers, and patent application described supra in the present application are hereby incorporated by reference in their entirety.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

REFERENCES

1. Aubert, M., and J. A. Blaho. 2001. Modulation of apoptosis during herpes simplex virus infection in human cells. Microbes Infect 3:859-66.
2. Aubert, M., and J. A. Blaho. 1999. The herpes simplex virus type 1 regulatory protein ICP27 is required for the prevention of apoptosis in infected human cells. J Virol 73:2803-13.
3. Aubert, M., and J. A. Blaho. 2003. Viral oncoapoptosis of human tumor cells. Gene Ther 10:1437-45.
4. Aubert, M., J. O'Toole, and J. A. Blaho. 1999. Induction and prevention of apoptosis in human HEp-2 cells by herpes simplex virus type 1. J Virol 73:10359-70.
5. Aubert, M., L. E. Pomeranz, and J. A. Blaho. 2007. Herpes simplex virus blocks apoptosis by precluding mitochondrial cytochrome c release independent of caspase activation in infected human epithelial cells. Apoptosis 12:19-35.
6. Goodkin, M. L., E. R. Morton, and J. A. Blaho. 2004. Herpes simplex virus infection and apoptosis. Intl Rev Immunol 23:141-72.
7. Jerome, K. R., Z. Chen, R. Lang, M. R. Torres, J. Hofmeister, S. Smith, R. Fox, C. J. Froelich, and L. Corey. 2001. HSV and glycoprotein J inhibit caspase activation and apoptosis induced by granzyme B or Fas. J Immunol 167:3928-35.
8. Jerome, K. R., R. Fox, Z. Chen, A. E. Sears, H. Lee, and L. Corey. 1999. Herpes simplex virus inhibits apoptosis through the action of two genes, Us5 and Us3. J Virol 73:8950-7.
9. Koyama, A. H., and A. Adachi. 1997. Induction of apoptosis by herpes simplex virus type 1. J Gen Virol 78:2909-12.
10. Koyama, A. H., and Y. Miwa. 1997. Suppression of apoptotic DNA fragmentation in herpes simplex virus type 1-infected cells. J Virol 71:2567-71.
11. Kraft, R. M., M. L. Nguyen, X. H. Yang, A. D. Thor, and J. A. Blaho. 2006. Caspase 3 activation during herpes simplex virus 1 infection. Virus Res 120:163-75.
12. Leopardi, R., and B. Roizman. 1996. The herpes simplex virus major regulatory protein ICP4 blocks apoptosis induced by the virus or by hyperthermia. Proc Natl Acad Sci USA 93:9583-7.
13. Leopardi, R., C. Van Sant, and B. Roizman. 1997. The herpes simplex virus 1 protein kinase US3 is required for protection from apoptosis induced by the virus. Proc Natl Acad Sci USA 94:7891-6.
14. Nguyen, M. L., and J. A. Blaho. 2007. Apoptosis during herpes simplex virus infection. Adv Virus Res 69:67-97.

15. Nguyen, M. L., R. M. Kraft, M. Aubert, E. Goodwin, D. DiMaio, and J. A. Blaho. 2007. p53 and hTERT determine sensitivity to viral apoptosis. J Virol 81:12985-95.
16. Nguyen, M. L., R. M. Kraft, and J. A. Blaho. 2005. African green monkey kidney Vero cells require de novo protein synthesis form efficient herpes simplex virus 1 dependent apoptosis. Virology 336:274-290.
17. Nguyen, M. L., R. M. Kraft, and J. A. Blaho. 2007. Susceptibility of cancer cells to herpes simplex virus dependent apoptosis. J. Gen. Virol. 88:1866-1875.
18. Sanfilippo, C. M., F. N. Chirimuuta, and J. A. Blaho. 2004. Herpes simplex virus type 1 immediate-early gene expression is required for the induction of apoptosis in human epithelial HEp-2 cells. J Virol 78:224-39.
19. Soliman, T. M., R. M. Sandri-Goldin, and S. J. Silverstein. 1997. Shuttling of the herpes simplex virus type 1 regulatory protein ICP27 between the nucleus and cytoplasm mediates the expression of late proteins. J Virol 71:9188-97.
20. Yedowitz, J. C., and J. A. Blaho. 2005. Herpes simplex virus 2 modulates apoptosis and stimulates NF-kappaB nuclear translocation during infection in human epithelial HEp-2 cells. Virology 342:297-310.

What is claimed is:

1. A method of determining susceptibility of a tumor cell to a chemotherapeutic agent, comprising the steps of:
    (a) providing a tumor cell isolated from a human suffering from a tumor, and said human is expected to receive a chemotherapeutic agent for treatment of said tumor;
    (b) infecting said provided tumor cell with a herpes simplex virus-1 lacking an immediate early gene, said immediate early gene is selected from the group consisting of ICP27, ICP4, and ICP22;
    (c) detecting a presence of one morphological alteration in said infected tumor cell, said morphological alteration in said infected tumor cell is selected from the group consisting of cell shrinkage, membrane blebbing, and chromatin condensation or a presence of death factor, said death factor is selected from the group consisting of poly(ADP-ribose) polymerase, caspase 3, and DNA fragmentation factor-45;
    (d) assessing the efficacy of a chemotherapeutic agent for treating said tumor in said human, said efficacy is determined by the presence of morphological alternation or the presence of death factor in said infected tumor cell, and said chemotherapeutic agent is selected from the group consisting of doxorubicin, etoposide, paclitaxel, cisplatin, and 5-fluorouracil, wherein the presence of said morphological alternation or death factor in said infected tumor cell is indicative of susceptibility of said tumor in said human being susceptible to said chemotherapeutic agent; and
    (e) providing to said human with said chemotherapeutic agent for treatment of said tumor, wherein said presence of morphological alteration or death factor is determined in said tumor cell.

2. The method of claim 1, wherein the absence of morphological alternation of said infected tumor cell is indicative of resistance of said tumor cell to said chemotherapeutic agent.

3. The method of claim 1, wherein said tumor cell is isolated from a source selected from the group consisting of breast, brain and cervix.

4. The method of claim 1, wherein said tumor cell is isolated from breast.

5. The method of claim 1, said infecting step is performed using a herpes simplex virus-1 lacking immediate early gene of ICP27.

6. The method of claim 1, wherein said morphological alternation is membrane blebbing.

7. The method of claim 1, wherein said morphological alternation is chromatin condensation.

8. The method of claim 1, wherein said death factor is DNA fragmentation factor-45.

9. The method of claim 1, wherein said death factor is poly(ADP-ribose) polymerase.

10. A method of using a herpes simplex virus reporter construct to assess efficacy of a chemotherapeutic agent, comprising the steps of:
    (a) providing a tumor cell isolated from a human suffering from a tumor and said human is expected to receive a chemotherapeutic agent for treatment of said tumor;
    (b) infecting said provided tumor cell with a herpes simplex virus containing a reporter construct, said reporter construct comprising a lacZ gene operably linked to an immediate early gene promoter, said immediate early gene promoter is selected from the group consisting of ICP27, ICP4, and ICP22;
    (c) detecting either a presence or an absence of lacZ gene activity of said reporter construct in said infected tumor cell;
    (d) assessing the efficacy of a chemotherapeutic agent in treating said tumor in said human, said efficacy is determined by the absence of lacZ gene activity of said reporter construct in said infected tumor cell, and said chemotherapeutic agent is selected from the group consisting of doxorubicin, etoposide, paclitaxel, cisplatin, and 5-fluorouracil, wherein said absence of negative lacZ gene activity is indicative of susceptibility of said tumor cell in said human being susceptible to said chemotherapeutic agent.

11. The method of claim 10, wherein said detecting step is performed by β-galactosidase staining.